United States Patent [19]

York, Jr.

[11] Patent Number: 4,609,663

[45] Date of Patent: Sep. 2, 1986

[54] ALDOSE REDUCTASE INHIBITORS USEFUL IN GLAUCOMA THERAPY

[75] Inventor: Billie M. York, Jr., Fort Worth, Tex.

[73] Assignee: Alcon Laboratories, Inc., Fort Worth, Tex.

[21] Appl. No.: 649,288

[22] Filed: Sep. 11, 1984

[51] Int. Cl.$^4$ ............... A61K 31/44; A61K 31/42; A61K 31/40; A61K 31/415

[52] U.S. Cl. ............... 514/278; 514/376; 514/398; 514/409; 514/913

[58] Field of Search ............. 514/278, 398, 376, 409, 514/913

[56] References Cited

U.S. PATENT DOCUMENTS

| | | | |
|---|---|---|---|
| 3,821,383 | 6/1974 | Sestanj | 424/258 |
| 4,117,230 | 9/1978 | Sarges | 548/309 |
| 4,130,714 | 12/1978 | Sarges | 548/309 |
| 4,181,728 | 1/1980 | Sarges et al. | 424/273 R |
| 4,209,630 | 6/1980 | Sarges | 548/309 |
| 4,226,875 | 10/1980 | Schnur | 548/216 |
| 4,307,108 | 12/1981 | Belletire et al. | 546/270 |
| 4,436,745 | 3/1984 | York, Jr. | 424/273 R |
| 4,438,272 | 3/1984 | York, Jr. | 424/273 R |
| 4,454,154 | 6/1984 | Matier | 424/311 |
| 4,455,317 | 6/1984 | Matier | 424/311 |
| 4,457,939 | 7/1984 | Schnur | 548/314 |
| 4,503,066 | 3/1985 | Brittain et al. | 514/409 |

OTHER PUBLICATIONS

Textbook of Medicine, vol. II—1975—p. 1606—W. B. Saunders Co. —Philadelphia, Pa.
Chem. Abst. 90: 166024(u) (1979)—Koraszewsku et al.
U.S. patent application Ser. No. 532,168, York, Jr.
Clinical Ophthalmology, vol. 3, Chapter 54, pp. 1 and 15-17 (1984).
Clinical Ophthalmology, vol. 3, Chapter 55, pp. 13-14 (1984).
Clinical Glaucoma, Chapter 9, pp. 129-130 (1977).
Early Primary Open-Angle Glaucoma: Diagnosis and Management, pp. 180-183 (1979).

*Primary Examiner*—Douglas W. Robinson
*Attorney, Agent, or Firm*—James A. Arno; Gregg C. Brown

[57] ABSTRACT

Method of treating glaucoma comprising the topical or systemic application of an aldose reductase inhibitor; compositions comprising such inhibitors are also disclosed.

8 Claims, No Drawings

ALDOSE REDUCTASE INHIBITORS USEFUL IN GLAUCOMA THERAPY

BACKGROUND OF THE INVENTION

This invention relates to methods and compositions useful in the therapy of primary open angle glaucoma. Specifically, this invention relates to compositions comprising an aldose reductase inhibitor; and methods of treatment comprising administering these compositions to treat the glaucoma syndrome, a leading cause of blindness.

While applicant is bound by no theory, it appears that an important mechanism underlying open angle glaucoma is one associated with the enzyme aldose reductase and/or related aldehyde reductases. Certain cells of the trabecular meshwork, lamina cribrosa and lamina vasculosa of the eye contain the enzyme aldose reductase and/or related aldehyde reductaces. These reductases under conditions of hyperglycemia or hyperglactosemia cause the accumulation of certain polyols such as sorbitol or galactitol respectively. The inhibition of the enzyme aldose reductase and related reductaces results in the retardation of abnormal polyol accumulation at the expense of NADPH in such ocular cells. Such inhibition preserves normal or near normal reduced glutathione status, $Na+/K+$ ATPase activity and amino acid transport within said cells. Furthermore, this inhibition promotes or preserves normal collagen production in and around these cells of the trabecular meshwork which are susceptible to high aldose concentrations. This includes cells of the lamina cribrosa and lamina vasculosa in mammalian eyes, particularly those of man. Trabecular meshwork cells are important in preserving proper aqueous humor outflow facility of the eye. Intraocular pressure or tension in part corresponds to outflow facility. In certain conditions of elevated intraocular pressure, the outflow of the trabecular meshwork may be impaired due to abnormal collagen metabolism and insufficient trabecular meshwork cell population. The rheological characteristics of the trabecular meshwork are linked to the normal functions of its cells.

Pathological alterations in collagen production and support in the posterior segments of the eye, which include the lamina cribrosa and lamina vasculosa, are associated with impaired retinal function and vision loss in glaucoma. This weakening of the posterior support structures of the eye is suggested to arise from abnormally elaborated collagen. Aldose reductase inhibitors, such as those disclosed in the present invention, have been demonstrated to prevent an abnormal elaboration of collagen associated with hyperglycemia and/or hypergalactosemia. Hyperglycemia is believed to be associated with the complications of glaucoma in diabetes mellitus patients. It follows that moderate glucose intolerance as is associated with aging may be contributory to glaucoma. Therefore, a potent aldose reductase inhibitor will have therapeutic utility in the therapy and/or prevention of glaucoma.

Thus, it is an object of the present invention to provide methods of treatment and pharmaceutical compositions which will retard or delay the progressive field of vision loss associated with glaucoma; wherein the active in such methods and compositions is an aldose reductase inhibitor.

DETAILED DESCRIPTION OF THE INVENTION

Aldose reductase inhibitors which are particularly suitable for the method of the present invention and pharmaceutical compositions comprising these inhibitors are disclosed in the following copending, commonly assigned U.S. patent applications: U.S. Patent Application Ser. No. 532,168 filed Sept. 14, 1983 now U.S. Pat. No. 4,537,892 and U.S. Patent Application Ser. No. 368,630 filed Apr. 15, 1982 now U.S. Pat. No. 4,436,745; similarly, attention is directed to the following U.S. Pat. Nos.: 4,438,272; 3,821,383; 4,117,230; 4,130,714; and 4,181,728. To the extent that these applications and patents disclose aldose reductase inhibitors which are useful in the practice of the present invention, they are incorporated herein by reference.

Particularly preferred inhibitors are representatively indicated by the following list:

a. Spiro-(7-fluoro-4H-indeno[1,2-b]thiophen-4,4'-imidazolidine)-2',5'-dione;
b. Spiro-(2-fluoro-9H-fluoren-9,4'-imidazolidine)-2',5'-dione;
c. Spiro-(2-fluoro-9H-fluoren-9,3'-succinimide);
d. Spiro-(7-fluoro-5H-indeno[1,2-b]-pyridin-5,4'-imidazolidine)-2',5'-dione;
e. Spiro-(7-chloro-5H-indeno[1,2-a]pyridin-9,4'-imidazolidine)-2',5'-dione;
f. Spiro-(7-chloro-9H-pyrrolo[1,2-a]indol-9,4'-imidazolidine)-2',5'-dione;
g. Spiro-(2,7-difluoro-9H-fluoren-9,4'-imidazolidine)-2',5'-dione;
h. Spiro-(2,7-difluoro-9H-fluoren-9,3'-succinimide);
i. Spiro-(2,7-difluoro-9H-fluoren-9,5'-oxazolidine)-2',4'-dione;
j. Spiro-(7-fluoro-5H-indeno[1,2-b]pyridine-5,3'-succinimide);
k. Spiro-(7-chloro-5H-indeno[1,2-b]pyridine-5,3'-succinimide);
l. Spiro-(7-methylthio-5H-indeno[1,2-b]pyridin-5,3'-succinimide).

The preferred route of administration for the compositions of the present invention is topically to the eye or per oral. The exact dosage regimen is left to the routine discretion of clinician taking into consideration the host's age, sex, weight, and his history accounting for or attributing to the glaucoma in question.

The most preferred compositions will have the aldose reductase inhibitor of choice present at a concentration ranging from 0.1% to 2.0 weight % in a vehicle selected from buffered water, aqueous buffered carbopol gel, or a perfluoroalkane-type vehicle which is fully disclosed and claimed in copending commonly assigned U.S. Patent Application Ser. No. 528,890 filed Sept. 2, 1983, which is incorporated herein by reference.

Typical systemic routes of administration are fully disclosed and claimed in copending commonly assign U.S. Patent Applications Ser. Nos. 368,630 (filed Apr. 15, 1982) now U.S. Pat. No. 4,436,745 and 532,168 (filed Sept. 14, 1983) now U.S. Pat. No. 4,537,892 which are incorporated herein by reference.

The following representative examples illustrate suitable pharmaceutical compositions for topical or oral delivery of the involved aldose reductase inhibitors for glaucoma therapy.

EXAMPLE 1

Gel composition for topical, ocular administration:

| Ingredient | % by weight |
|---|---|
| 0.25% w/v of the compound Spiro-(7-chloro-5H—indeno[1,2-b]-pyridin-5,4'-imidazolidine)-2',5'-dione | 0.25% |
| Benzalkonium Chloride | 0.01% |
| Carboxypolymethylene (carbopol) | 1.0% |
| Hydrochloric Acid and/or Sodium hydroxide | to adjust pH to 5.0 to 5.5 |
| Purified Water q.s. to (as gel) | 100% |

The following topical, ocular formulations are physically in the form of suspensions:

| Suspension A | |
|---|---|
| Ingredient | % by weight |
| Micronized Spiro-(2-fluoro-9H—fluoren-9,4'-imidazolidine)-2',5-dione | 1.0% |
| Perfluorotributylamine | 99.0% |

| Suspension B | |
|---|---|
| Ingredient | % by weight |
| Micronized Spiro-(2,-7-difluoro-9H—fluoren-9,3'-succinimide) | 1.0% |
| Hydroxymethylcellulose | 1.0% |
| Disodium edetate | 0.01% |
| Benzalkonium chloride | 0.01% |
| Sodium Acetate | 0.14% |
| Sodium Chloride | 0.52% |
| Hydrochloric Acid and/or Sodium Hydroxide | ph 4.5 to 5.5 |
| Purified Water (as suspension) q.s. to | 100% |

The following formulation is a selected representative of a solution for the ophthalmic indications of the present invention:

| Ingredient | % by weight |
|---|---|
| Spiro-(7-fluoro-5H—indeno[1,2-b]pyridine-5,3'-succinimide) | 0.10% |
| Carboxypolymethylene (carbopol) | 0.10% |
| Benzalkonium Chloride | 0.008% |
| Hydrochloric Acid and/or Sodium Hydroxide | to adjust pH 4.5 to 5.0 |
| Purified Water q.s. to | 100% |

EXAMPLE 2

A dry solid pharmaceutical composition is prepared by mixing the following materials together in the proportions by weight specified:

| Ingredient | % by weight |
|---|---|
| Micronized Spiro-(2,7-difluoro-9H—fluoren-9,4'-imidazolidine)-2',5'-dione | 50% |
| Sodium Citrate | 20% |
| Alginic Acid | 5% |
| Polyvinylpyrrolidone | 15% |
| Magnesium Stearate | 5% |

The dry composition is thoroughly blended, tablets are punched from the resulting mixture, each tablet being of such size that it contains 100 mg of the active ingredient. Other tables are also prepared in a likewise manner containing 10, 25 and 200 mg of active ingredient, respectively, by merely using an appropriate quantity by weight of the spiro-hydantoin in each case. Likewise other related examples of spiro-imidazolidinediones, spiro-thiazolidinediones, spiro-oxazolidinediones, spiro-succinimides can be formulated as tablets on a respective weight proportion.

The dry solid pharmaceutical composition is prepared by combining the following materials together in the weight proportions indicated below:

| Ingredient | % by weight |
|---|---|
| Spiro-(7-fluoro-5H—indeno[1,2-b]pyridin-5,4'-imidazolidine)-2',5'-dione | 50% |
| Calcium Carbonate | 20% |
| Polyethylene glycol, Average Molecular Weight 8,000 | 30% |

The dried solid mixture is thoroughly mixed until uniform in composition. The powdered product is then used to fill soft elastic and hard-gelatin capsules so as to provide capsules containing 200 mg of the active ingredient.

What is claimed is:

1. A method of treating the eye of a patient to retard or delay the progressive field of vision loss associated with primary open angle glaucoma which comprises the topical, oral or systemic administration of a therapeutically effective amount of a pharmaceutical composition containing an aldose reductase inhibitor.

2. A method according to claim 1 wherein the patient is human and diabetic.

3. A method according to claim 1 wherein the patient is human and exhibits ocular hypertension.

4. A method according to claim 1, wherein the aldose reductase inhibitor is selected from the group consisting of:

a. Spiro-(7-fluoro-4H-indeno[1,2-b]thiophen-4,4'imidazolidine)-2',5'-dione;

b. Spiro-(2-fluoro-9H-fluoren-9,4'1-imidazolidine)-2',5'-dione;

c. Spiro-(2-fluoro-9H-fluoren-9,3'-succinimide);

d. Spiro-(7-fluoro-5H-indeno[1,2-b]-pyridin-5,4'-imidazolidine)-2',5'-dione;

e. Spiro-(7-chloro-5H-indeno[1,2-b]-pyridin-5,4'-imidazolidine)-2',5'-dione;

f. Spiro-(7-chloro-9H-pyrrolo[1,2-a]indol-9,4'-imidazolidine)-2',5'-dione;

g. Spiro-(2,7-difluoro-9H-fluoren-9,4'-imidazolidine)-2',5'-dione;
h. Spiro-(2,7-difluoro-9H-fluoren-9,3'-succinimide);
i. Spiro-(2,7-difluoro-9H-fluoren-9,5'-oxazolidine)-2',4'-dione;
j. Spiro-(7-fluoro-5H-indeno[1,2-B]pyridine-5,3'-succinimide);
k. Spiro-(7-chloro-5H-indeno[1,2-B]pyridine-5,3'-succinimide); and
l. Spiro-(7-methylthio-5H-indeno[1,2-b]pyridin-5,3'-succinimide).

5. A method according to claim 2 wherein the aldose reductase inhibitor is selected from the group consisting of:
a. Spiro-(7-fluoro-4H-indeno[1,2-b]thiophen-4,4'imidazolidine)-2',5'-dione;
b. Spiro-(2-fluoro-9H-fluoren-9,4'1-imidazolidine)-2',5'-dione;
c. Spiro-(2-fluoro-9H-fluoren-9,3'-succinimide);
d. Spiro-(7-fluoro-5H-indeno[1,2-b]-pyridin-5,4'-imidazolidine)-2',5'-dione;
e. Spiro-(7-chloro-5H-indeno[1,2-b]-pyridin-5,4'-imidazolidine)-2',5'-dione;
f. Spiro-(7-chloro-9H-pyrrolo[1,2-a]indol-9,4'-imidazolidine)-2',5'-dione;
g. Spiro-(2,7-difluoro-9H-fluoren-9,4'-imidazolidine)-2',5'-dione;
h. Spiro-(2,7-difluoro-9H-fluoren-9,3'-succinimide);
i. Spiro-(2,7-difluoro-9H-fluoren-9,5'-oxazolidine)-2',4'-dione;
j. Spiro-(7-fluoro-5H-indeno[1,2-B]pyridine-5,3'-succinimide);
k. Spiro-(7-chloro-5H-indeno[1,2-B]pyridine-5,3'-succinimide); and
l. Spiro-(7-methylthio-5H-indeno[1,2-b]pyridin-5,3'-succinimide).

6. A method according to claim 3 wherein the aldose reductase inhibitor is selected from the group consisting of:
a. Spiro-(7-fluoro-4H-indeno[1,2-b]thiophen-4,4'imidazolidine)-2',5'-dione;
b. Spiro-(2-fluoro-9H-fluoren-9,4'1-imidazolidine)-2',5'-dione;
c. Spiro-(2-fluoro-9H-fluoren-9,3'-succinimide);
d. Spiro-(7-fluoro-5H-indeno[1,2-b]-pyridin-5,4'-imidazolidine)-2',5'-dione;
e. Spiro-(7-chloro-5H-indeno[1,2-b]-pyridin-5,4'-imidazolidine)-2',5'-dione;
f. Spiro-(7-chloro-9H-pyrrol[1,2-a]indol-9,4'-imidazolidine)-2',5'-dione;
g. Spiro-(2,7-difluoro-9H-fluoren-9,4'-imidazolidine)-2',5'-dione;
h. Spiro-(2,7-difluoro-9H-fluoren-9,3'-succinimide);
i. Spiro-(2,7-difluoro-9H-fluoren-9,5'-oxazolidine)-2',4'-dione;
j. Spiro-(7-fluoro-5H-indeno[1,2-B]pyridine-5,3'-succinimide);
k. Spiro-(7-chloro-5H-indeno[1,2-B]pyridine-5,3'-succinimide); and
l. Spiro-(7-methylthio-5H-indeno[1,2-b]pyridin-5,3'-succinimide).

7. A method according to claim 1 wherein the aldose reductase inhibitor is contained in a concentration ranging from 0.1 to 2.0 weight % in a vehicle.

8. A method according to claim 7 wherein the vehicle is selected from the group consisting of buffered water, aqueous buffered carbopol gel, and a perfluoroalkane.

* * * * *